United States Patent [19]
Umezawa et al.
[11] 4,127,714
[45] Nov. 28, 1978

[54] ANTHRACYCLINE GLYCOSIDES

[75] Inventors: Hamao Umezawa; Tomio Takeuchi, both of Tokyo; Masa Hamada, Hoya; Masaaki Ishizuka; Hiroshi Naganawa, both of Tokyo; Toshikazu Oki, Kamakura; Taiji Inui, Chigasaki, all of Japan

[73] Assignee: Zaidan Hojin Biseibutsu Kagaku Kenkyu Kai, Tokyo, Japan

[21] Appl. No.: 823,052

[22] Filed: Aug. 9, 1977

[30] Foreign Application Priority Data

Aug. 16, 1976 [JP] Japan .................................. 51-98113

[51] Int. Cl.$^2$ .............................................. C07H 15/24
[52] U.S. Cl. .................................... 536/17; 195/80 R; 424/180; 536/4
[58] Field of Search ............................ 536/17 A, 17, 4

[56] References Cited

U.S. PATENT DOCUMENTS

| | | | |
|---|---|---|---|
| 3,988,315 | 10/1976 | Umezawa et al. | 536/17 A |
| 4,039,736 | 8/1977 | Nettleton, Jr. et al. | 536/17 A |

OTHER PUBLICATIONS

Keller-Schierlein et al., "Antimicrobial Agents and Chemotherapy", 1970, pp. 68-77.

*Primary Examiner*—Johnnie R. Brown
*Attorney, Agent, or Firm*—David M. Morse

[57] ABSTRACT

New antitumor agents designated rhodirubin A and B, which are anthracycline glycosides and inhibit the growth of gram-positive bacteria and mammalian tumors, are produced by fermentation of rhodirubin-producing strains of Streptomyces, e.g. *Streptomyces sp.* ME 505-HEI (ATCC 31273).

7 Claims, No Drawings

ANTHRACYCLINE GLYCOSIDES

BACKGROUND OF THE INVENTION

1. Field of the Invention

This invention relates to new anthracycline glycoside antitumor antibiotics, to methods for their preparation and recovery, to pharmaceutical compositions containing them and to methods of using said antibiotics as antibacterial and antitumor agents.

2. Description of the Prior Art

A number of anthracycline glycosides have been described in the literature. Among them, daunomycin and adriamycin have already been applied clinically for treatment of human cancers. Preparation of adriamycin by fermentation of *S. peuceticus var. caesius* is disclosed in U.S. Pat. No. 3,590,029. Chemical conversion of daunomycin to adriamycin is taught in U.S. Pat. No. 3,803,124. Daunomycin (produced by fermentation of *S. peuceticus* in U.K. Pat. No. 1,003,383) may be the same as Rhone-Poulenc's 13,057 R.P. (formerly rubidomycin and now daunorubicin; see U.K. Pat. No. 985,598, 1,188,262 and 1,241,750 and U.S. Pat. No. 3,616,242) and is probably identical to Ciba's danubomycin disclosed in U.S. Pat. No. 3,092,550 and U.K. Pat. No. 901,830. See also U.S. Pat. No. 3,092,550 and U.K. Pat. No. 901,830. See also U.S. Pat. No. 3,686,163 on dihydrodaunomycin.

Cinerubin A and cinerubin B, glycosides of the aglycone, ε-pyrromycinone, are disclosed in U.K. Pat. No. 846,130 [see also U.S. Pat. No. 3,864,480 and Keller-Schierlein *et al., Antimicrobial Agents and Chemotherapy*, page 68 (1970) and *Chemical Abstracts*, 54, 1466i (1960)].

Aclacinomycin A and B having the aglycone, aklavinone, are disclosed in U.S. Pat. No. 3,988,315.

The anthracycline glycoside, carminomycin, described in *J. Antibiotics*, 27, 254-259 (1974), in *J. Amer. Chem. Soc.*, 97 (20), 5955-5956 (1975) and in U.K. Pat. No. 1,426,637 has been reported to be active against several animal tumor systems.

Pyrromycin, an anthracycline glycoside containing the aglycone, ε-pyrromycinone, and the glycosidic sugar, rhodosamine, is disclosed in *Chem. Ber.*, 92, 1904-1909 (1959).

Galirubin A having the aglycone, ε-pyrromycinone, is disclosed in *Chemical Abstracts*, 64, 3896g (1966) and *Chemical Abstracts*, 67, 90573z (1967).

Rutilantin having the aglycone, ε-pyrromycinone, is disclosed in *Biochem. J.*, 81, 101-104 (1961).

For further illustrative and summary disclosures of anthracycline antibiotics see *Index of Antibiotics from Actinomycetes*, Hamao Umezawa, Editor-in-chief, University Park Press, State College, Penn., U.S.A. (1967) as follows:

| Antibiotic | Page No. |
|---|---|
| Aklavin | 111 |
| Cinerubin A | 220 |
| Cinerubin B | 221 |
| Danubomycin | 242 |
| Daunomycin | 243 |
| Pyrromycin | 542 |
| Rhodomycin A,B | 561 |
| Rubidomycin | 574 |

The textbook *Antibiotics*, Volume 1, Mechanism of Action, edited by David Gottlieb and Paul D. Shaw, Springer-Verlag New York, Inc., New York, New York (1967) at pages 190–210 contains a review by A. DiMarco entitled "Daunomycin and Related Antibiotics".

Information Bulletin, No. 10, International Center of Information of Antibiotics, in collaboration with WHO, December, 1972, Belgium, reviews anthracyclines and their derivatives.

SUMMARY OF THE INVENTION

This invention relates to novel anthracycline glycoside antibiotics designated herein as rhodirubin A and B. The antibiotics are obtained by cultivating a rhodirubin-producing strain of Streptomyces in an aqueous nutrient medium under submerged aerobic conditions until a substantial amount of rhodirubin is produced by said microorganism in said culture medium and, optionally, recovering the rhodirubin from the culture medium. Rhodirubin A and B may be recovered from the culture medium and separated by extraction of the broth, with or without the prior separation of mycelia, or by extraction from mycelia followed by separation and purification of the individual antibiotics by standard procedures used to isolate and purify other water-insoluble antibiotics. This invention embraces rhodirubin A and B as crude solids, as purified solids, as their salts with organic or inorganic acids and as DNA-complexes.

There is thus provided by the present invention the antitumor antibiotics rhodirubin A and B having the formulae

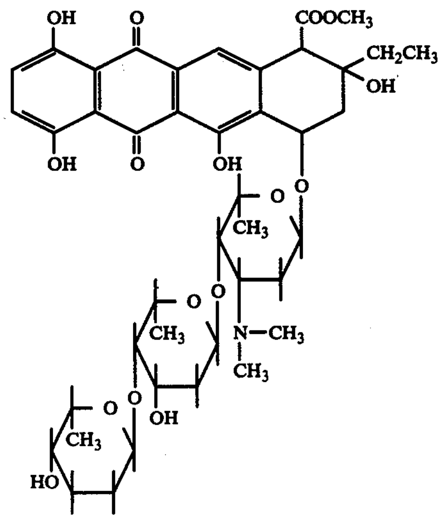

rhodirubin A and

-continued

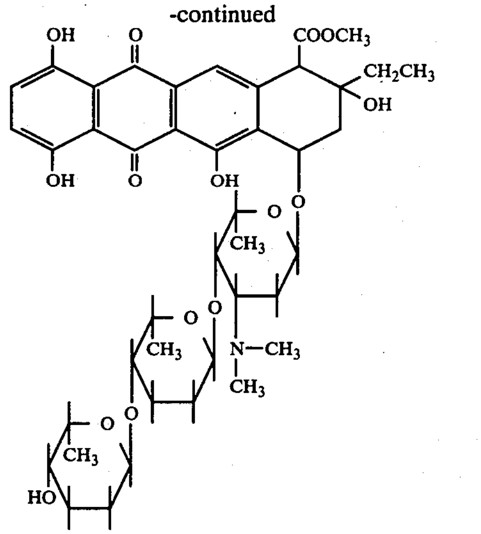

rhodirubin B and the non-toxic acid addition salts and complexes thereof with deoxyribonucleic acid.

Rhodirubin A and B have been found to possess both antimicrobial and antitumor activity. More particularly, the compounds of the present invention exhibit antimicrobial activity against gram-positive bacteria, inhibit the growth of solid and ascitic forms of malignant tumors in mammals, e.g. mouse leukemia L1210, possess a high cytotoxicity and thus inhibit the growth of mammalian tumor cells in culture and exhibit low toxicity.

As used herein the term rhodirubin refers to the antibiotic which includes at least one antibiotic selected from rhodirubin A and B.

DETAILED DESCRIPTION

The compounds of the present invention are produced by fermentation of various rhodirubin-producing strains of Streptomyces including several known pyrromycin-, cinerubin-, aclacinomycin- and galirubin-producing strains such as *Streptomyces galilaeus* MA 144-M (ATCC 31133, FERM P-2455), *Streptomyces galilaeus* (ATCC 14969), *Streptomyces cinereoruber* (ATCC 19740), *Streptomyces antibioticus (ATCC* 8663), *Streptomyces purpurasceus* (ATCC 25489) and *Streptomyces niveoruber* (ATCC 14971).

A preferred rhodirubin-producing strain of Streptomyces has been isolated by the present inventors from a soil sample collected at the campus of the Institute of Microbial Chemistry at Osaki, Shinagawa-ku, Tokyo, Japan, and cultures of this strain designated strain ME 505-HEI have been deposited in the American Type Culture Collection, Rockville, Maryland and in the Fermentation Research Institute, Japan, and added to their permanent collections of microorganisms as ATCC 31273 and FERM P-3667, respectively.

Characteristics of *Streptomyces sp.* ME 505-HEI are under investigation in detail. The strain No. ME 505-HEI has the following characteristics at present: Under the microscope, the aerial mycelia have no verticillate branch and no spiral structure. The growth on the various media is found to be colorless, pale reddish brown to dark brownish purple, and aerial mycelium is not formed or is formed slightly with white to pinkish white color. Dull red soluble pigment is slightly formed. Melanine formation is positive. Based on the above characteristics, strain ME 505-HEI belongs to the genus Streptomyces.

Since the Streptomyces are easily mutated naturally or artificially, Streptomyces ME 505-HEI and the other rhodirubin-producing Streptomyces of the present invention include the typical strains described above and all natural and artificial rhodirubin-producing variants and mutants thereof.

Production of the compounds of the present invention is carried out by cultivating a rhodirubin-producing strain of Streptomyces in a conventional aqueous nutrient medium containing known nutritional sources for actinomycetes, i.e. assimilable sources of carbon and nitrogen plus optional inorganic salts and other known growth factors. Submerged aerobic culture is preferably used for the production of large quantities of the antibiotics, although for production of limited amounts surface cultures and bottles can also be employed. Media consisting of known kinds of nutritional sources for actinomycetes are useful, and the general procedures used for the cultivation of other actinomycetes are applicable to the present invention. The medium preferably contains commercially available products such as glucose, glycerol, starch, dextrin, sucrose, maltose and the like as the carbon source with other carbohydrates, alcohols, organic acids, oils and fats in either purified or crude state also being employable for this purpose depending on the assimilability of the strain. Commercially available products such as soybean meal, cotton-seed flour, meat extract, peptone, dried yeast, yeast extract, corn steep liquor and the like are preferably employed as organic nitrogen sources and inorganic salts such as $(NH_4)_2SO_4$, $NaNO_3$, $NH_4Cl$ and the like as inorganic nitrogen sources. There may also be added, if necessary, inorganic salts such as chlorides (NaCl or KCl) or phosphates, trace metals (e.g. zinc, magnesium, manganese, cobalt, iron and the like) or defoamers such as Adekanol (trademark of Asahi Denka Ind. Co.), Silicone (trademark of Shinetsu Chem. Ind. Co.), liquid paraffin, soybean oil or fat. The culture temperature should be in the range of about 20° C. to 37° C., preferably about 25° C. to 30° C. The pH of the culture medium normally ranges from about 5 to 8. Production of rhodirubin in the culture broth usually reaches a maximum about 3 to 7 days after inoculation.

A variety of known procedures can be employed in the isolation and purification of the rhodirubin compounds from the fermentation medium, for example, solvent extraction, solvent precipitation, concentration, gel filtration, counter current distribution, chelation with metal ions, adsorption followed by elution from an ion-exchange resin, adsorbent siliceous earth material or synthetic adsorbent, or a combination of one or more of the above-described procedures.

In a preferred recovery process the rhodirubin A and B are recovered from the culture medium by solvent extraction. The rhodirubin antibiotics exist intracellularly as well as extracellularly, but are found mainly in the mycelium. Advantageously the mycelia are first separated from the filtrate of the culture broth by conventional means such as filtration or centrifugation, although the antibiotics may also be extracted directly from the culture broth by the procedures discussed below without separation of the mycelia. Rhodirubin A and B may be extracted from the filtrate at neutral or weakly basic pH (e.g. pH 7-9) with a water-immiscible organic solvent such as ethyl acetate, butyl acetate, chloroform, n-butanol, etc. Rhodirubin A and B in the mycelia may be extracted with an organic solvent such as chloroform, ethyl acetate, n-butanol, methanol, acetone or methyl ethyl ketone or an aqueous solution of an organic or inorganic acid such as hydrochloric acid or acetic acid. The active rhodirubin extracts are then concentrated and dried in vacuo to obtain a reddish or reddish-purple powder which is a mixture of crude rhodirubin A and B.

To separate the individual rhodirubin A and B components from the crude mixture, further purification and separation techniques such as column chromatography with adsorbents like silica gel, modified dextrans (e.g. Sephadex LH-20 - trademark of Pharmacia Fine Chemicals, Sweden), weakly acidic ion-exchange resins, activated carbon or alumina, countercurrent distribution or liquid chromatography with suitable organic solvents. As an example of a suitable separation procedure, crude rhodirubin powder (mixture of A and B components) may be dissolved in toluene-methanol, subjected to column chromatography over silica gel and eluted with a suitable organic solvent such as toluene-methanol to give the individual rhodirubin A and B components. The active eluates containing the rhodirubin A and B are concentrated under reduced pressure, and the individual components then further purified by chromatography over Sephadex LH-20.

Solutions of purified rhodirubin A and B may also be lyophilized after the addition of one or more substances selected from deoxyribonucleic acid, glycerol, sugars, amino acids and organic or inorganic acids.

Physicochemical Properties of Rhodirubin A and B

The physicochemical properties of rhodirubin A and B are as follows:

Rhodirubin A

Red powder having a melting point of 141°-143° C. Elementary analysis yields the following values:

| | | Calcd for $C_{42}H_{55}NO_{16}$ |
|---|---|---|
| Found | C = 60.39% | C = 60.77% |
| | H = 6.63% | H = 6.68% |
| | O = 30.72% | O = 30.81% |
| | N = 1.71% | N = 1.69% |

Molecular weight: 829.9. Specific rotation: $[\alpha]_D^{20}$ + 120 (C = 0.1, $CHCl_3$). Solubility: Rhodirubin A is soluble in methanol, n-butanol, acetone, ethyl acetate, chloroform, toluene, benzene and dimethylsulfoxide, insoluble in water, n-hexane and petroleum ether and slightly soluble in diethyl ether.

Color and reaction: The methanol solution of rhodirubin A is red, but turns to reddish purple in the alkaline state. It gives a negative ninhydrin reaction and does not reduce Fehling solution.

Absorption spectrum: Ultraviolet and visible absorption maxima are seen at 235 nm, $E_{1cm}^{1\%}$ = 507; 258 nm, $E_{1cm}^{1\%}$ = 267; 295 nm, $E_{1cm}^{1\%}$ = 100; 457 nm, $E_{1cm}^{1\%}$ = 127; 490 nm, $E_{1cm}^{1\%}$ = 153; 510 nm, $E_{1cm}^{1\%}$ = 117; 522 nm, $E_{1cm}^{1\%}$ = 100 (in methanol at a concentration of 15 mcg./ml.)

Absorption spectrum: Infrared: The IR spectrum in KBr shows peaks at the following wavelengths in $cm^{-1}$: 3430, 2950, 2930, 2810, 2750, 1735, 1640, 1600, 1450, 1320, 1300, 1220, 1160, 1120, 1040, 1000, 970, 960, 920, 800 and 760.

NMR: The PMR spectrum of rhodirubin A in $CDCl_3$ (100 MHz) shows the following chemical shifts (ppm): 7.6, s; 7.24, s; 5.50, m; 5.62, m; 5.02, m; 4.84, m; 4.52, q; 4.7 ~ 3.90, overlapping m; 3.72, s; 3.60 ~ 0.09, overlapping m and 2.18

Rhodirubin B

Red powder having a melting point of 135°-137° C. Elementary analysis yields the following values:

| | | Calcd. for $C_{42}H_{55}NO_{15}$ |
|---|---|---|
| Found: | C = 61.23% | C = 61.99% |
| | H = 6.80% | H = 6.77% |
| | O = 28.77% | O = 29.52% |
| | N = 1.94% | N = 1.72% |

Molecular weight = 813.9. Specific rotation = $[\alpha]_D^{20}$ + 190 (C = 0.1, $CHCl_3$)

Solubility: Rhodirubin B is soluble in methanol, n-butanol, acetone, chloroform, ethyl acetate, toluene, benzene and dimethylsulfoxide, insoluble in water, petroleum ether and n-hexane and slightly soluble in diethyl ether.

Color and reaction: The methanol solution of rhodirubin B is red, but turns to reddish purple in the alkaline state. It gives a negative ninhydrin reaction and does not reduce Fehling solution.

Absorption spectrum: Ultraviolet and visible absorption maxima are seen at 235 nm, $E_{1cm}^{1\%}$ = 593; 257 nm, $E_{1cm}^{1\%}$ = 307; 295 nm, $E_{1cm}^{1\%}$ = 113; 457 nm, $E_{1cm}^{1\%}$ = 153; 490 nm, $E_{1cm}^{1\%}$ = 187; 510 nm, $E_{1cm}^{1\%}$ = 147; 522 nm, $E_{1cm}^{1\%}$ = 120

Absorption spectrum: Infrared. The IR spectrum in KBr shows peaks at the following wavelengths in $cm^{-1}$: 3470, 2960, 2940, 2820, 2790, 1740, 1640, 1600, 1450, 1300, 1220, 1160, 1120, 1040, 1000, 980, 960, 920, 800, 790 and 760.

NMR: The PMR spectrum of rhodirubin B in $CDCl_3$ (100 MHz) shows the following chemical shifts (ppm): 7.6, s; 7.24, s; 5.50, m; 5.02, m; 4.84, m; 4.52, q; 4.7 ~ 3.90, overlapping m; 3.72, s; 3.6 ~ 0.09, overlapping m and 2.18, s.

Rhodirubin A and B have the following $R_f$ values on silica gel thin-layer chromatograms using the indicated solvent systems:

| | $R_f$ Values | |
|---|---|---|
| Solvent System | Rhodirubin A | Rhodirubin B |
| ethyl:acetate:benzene: methanol (5:5:1) (v/v) | 0.37 | 0.42 |
| chloroform:methanol (10:1) (v/v) | 0.19 | 0.28 |
| chloroform:methanol (10:1) (v/v) | 0.17 | 0.20 |

Structure Determination

The structures of rhodirubin A and B were determined as follows: Aglycones of rhodirubin A and B were obtained by acid hydrolysis with dilute hydrochloric acid (0.1N) at 85° C. for 30 min. Physico-chemical properties, e.g. IR, UV, NMR, melting point and $R_f$ values on thin layer chromatography, of the aglycones obtained coincided fully with those of ε-pyrromycinone described in the literature [Chem. Ber., 92, 1904 (1959)].

After neutralizing and concentrating the aqueous layer of the rhodirubin A and B hydrolyzates, the sugar moiety was developed and separated by thin layer chromatography (silica gel TLC, Merck $F_{254}$:solvents:-butanol:acetic acid:water = 4:1:1) (v/v). Three sugar moieties ($R_f$ = 0.14: 0.53:0.67) were obtained from rhodirubin A and two sugar moieties ($R_f$ = 0.14:0.67) from rhodirubin B. By comparing these with the sugars obtained from aclacinomycin [*J. Antibiotics*, 28, 830–834 (1975)] and streptolydizin [*J. Am. Chem. Soc.*, 86, 3592-3594 (1964)], the various color reactions [Pharmazie, 27, H12, 782-789 (1972)], specific rotations and NMR, the sugars having $R_f$ = 0.14, 0.53 and 0.67 were identified to be rhodosamine, 2-deoxyfucose and rhodinose, respectively.

Methanolysis of rhodirubin A or B gave pyrromycin (rhodosaminyl ϵ-pyrromycinone). Furthermore, rhodinose was liberated from rhodirubin A or B by a mild hydrolysis (0.5% HCl, 20° C., 10 minutes) according to the method disclosed in *Naturwise*, 50, 43-44 (1963).

From the results described above, the structures of rhodirubin A or B in the present invention were determined to be as follows:

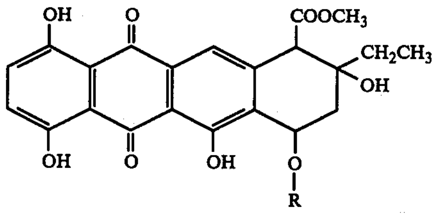

wherein R represents rhodirubin A
R is

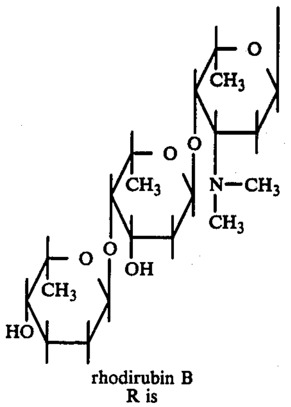

rhodirubin B
R is

-continued

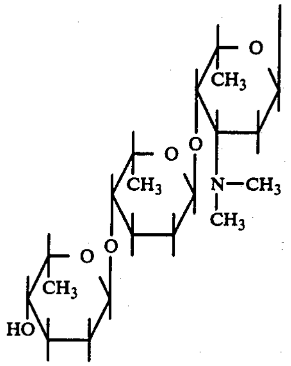

Among anthracycline antibiotics described in the literature, cinerubin, aclacinomycin, violamycin and rhodomycin are known to consist of an aglycone and three sugar moieties. Their constituents are shown below:

| Antibiotics | Aglycone | Binding position of sugar and aglycone | First sugar | Second sugar | Third sugar |
|---|---|---|---|---|---|
| cinerubin A | ϵ-pyrromycinone | 7 | rhodasamine | 2-deoxy-fucose | cinerulose |
| aclacino-mycin A | alkavinone | 7 | rhodosamine | " | " |
| violamycin | various rhodamycinone | unknown | rhodosamine | " | rhodonose |
| rhodomycin X | -rhodomycinone -rhodomycinone 10-deoxy-r-rhodomycinone | 9- or 10- | rhodosamine | " | " |

It will be seen that the rhodirubin antibiotics are readily distinguishable from the above anthracyclines.

Antibiotic Activity of Rhodirubin A and B

Rhodirubin A and B exhibit antimicrobial activity against various microorganisms. The minimum inhibitory concentration of rhodirubin A and B as determined by the broth dilution method are shown in the table below:

Minimum Inhibitory Concentration of Rhodiribum A and B

| Test microorganism | MIC (mcg./ml.) rhodirubin A | Rhodirubin B |
|---|---|---|
| *Staph. aureus* FDA 209P | 1.56 | 1.56 |
| *Staph. aureus* Smith | 0.4 | 0.78 |
| *B. subtilis* ATCC 6633 | 0.78 | 1.56 |
| *B. cereus* ATCC 9634 | 0.2 | 0.4 |
| *B. megaterium* NRRL-938 | 0.78 | 1.56 |
| *Sarcina lutea* ATCC 9341 | 0.4 | 0.78 |
| *Micrococcus flavus* | 0.2 | 0.2 |
| *Coryne: bovis* | 0.2 | 0.4 |
| *Ps. fluorescens* NIHJB-254 | 100 | 100 |
| *Proteus morganii* | >100 | >100 |
| *Mycobacterium smegmatis* ATCC 607 | 6.25 | 3.1 |
| *Candida albicans* IAM 4905 | >100 | >100 |
| *Candida tropicalis* IAM 4942 | >100 | >100 |

As shown above, rhodirubin A and B possess antimicrobial activity, especially against gram-positive bacteria, and thus they are therapeutically useful in the treatment of animals, including man, for infectious diseases caused by such microorganisms.

Antitumor Activity of Rhodirubin A and B

Rhodirubin A and B show a marked antitumor activity with low toxicity in experimental animal tests and thus are therapeutically useful in inhibiting the growth of animal tumors. In particular, rhodirubin A and B show marked inhibitory effects on mouse L1210 leukemia. For example, $CDF_1$ mice were inoculated intraperitoneally with $1 \times 10^6$ L1210 cells/mouse and 0.1–0.2 ml. of drug solution then administered intraperitoneally for 10 consecutive days. Observation was carried out for 30 days, and the % of prolongation of survival time to the control mice intraperitoneally administered with physiological saline was as follows:

| Dosage (mg./kg./day) | Prolongation of the survival time T/C (%) | |
|---|---|---|
| | rhodirubin A (HCl salt) | rhodirubin B (HCl salt) |
| 10 | 87 | 104 |
| 8.5 | 121 | 160 |
| 5 | 195 | 179 |
| 2.5 | 167 | 215 |
| 1.25 | 117 | 126 |
| 0.6 | 102 | 107 |

Acute Toxicity

The $LD_{50}$ values upon intraperitoneal injection (in mice) of rhodirubin A and B are as follows:

| | $LD_{50}$ (mg./kg.) |
|---|---|
| rhodirubin A | 7.5 - 10 |
| rhodirubin B | 10 - 12.5 |

The Therapeutic Use of Rhodirubin A and B

As noted above, the compounds rhodirubin A and B in the present invention are novel antibacterial agents, useful in both human and veterinary medicine, and antitumor agents possessing marked inhibitory action against malignant tumors in animals, including both ascitic and solid tumors.

The compounds in the present invention form non-toxic acid addition salts with a variety of organic and inorganic salt-forming reagents and form non-toxic complexes with deoxyribonucleic acid. Thus, acid addition salts formed with such pharmaceutically acceptable acids as sulfuric, phosphoric, hydrochloric, acetic, propionic, oleic, palmitic, citric, succinic, tartaric, glutamic, pantothenic, etc. and non-toxic complexes with deoxyribonucleic acid can be employed in the same manner as the rhodirubin compounds per se. The salts are formed, isolated, purified and formulated by the methods generally employed in salt formation for antibiotics. In the case of the DNA complexes, DNA extracted from animals and microorganisms such as calf thymus, Hela cells, human and animal embryonic cells, yeasts, etc. can be used. Preparation of rhodirubin-DNA complexes can be carried out by methods described in the literature for preparing DNA complexes of other anthracycline antibiotics such as adriamycin, daunorubicin, etc. [see, for example, *Nature, New Biol.*, 239, 110 (1973) and *Europ. J. Cancer*, 10, 399 (1974)]. For purposes of this invention, the rhodirubin compounds in the free base form are equivalent to their non-toxic acid addition salts and DNA-complexes.

According to another aspect of this invention, a method is provided for therapeutically treating an animal host affected by a gram-positive bacterial infection or by a malignant tumor (i.e. a solid or ascitic-type tumor such as L1210 leukemia) which comprises administering to said host an effective antibacterial or tumor-inhibiting dose of rhodirubin A or B, or a mixture thereof, or a non-toxic acid addition salt or DNA-complex thereof.

According to another aspect of this invention, a pharmaceutical composition is provided which comprises an effective antibacterial or tumor-inhibiting amount of rhodirubin A or B, or a mixture thereof, or a non-toxic acid addition salt or DNA-complex thereof, in combination with an inert pharmaceutically acceptable carrier or diluent. These compositions may be made up in any pharmaceutical form appropriate for parenteral administration.

Preparations according to the invention for parenteral administration include sterile aqueous or non-aqueous solutions, suspensions or emulsions. They may also be manufactured in the form of sterile solid compositions which can be dissolved in sterile water, physiological saline or some other sterile injectable medium immediately before use.

It will be appreciated that the actual preferred amounts of the rhodirubin antibiotic used will vary according to the particular compound being used, the particular composition formulated, the mode of application and the particular situs, host and disease being treated. In general the rhodirubin antibiotics are injected intraperitoneally, intravenously, subcutaneously or locally into animals and intravenously or locally into humans. Many factors that modify the action of the drug will be taken into account by those skilled in the art, for example, age, body weight, sex, diet, time of administration, route of administration, rate of excretion, condition of the patient, drug combinations, reaction sensitivities and severity of the disease. Administration can be carried out continuously or periodically within the maximum tolerated dose. Optimal application rates for a given set of conditions can be ascertained by those skilled in the art using conventional dosage determination tests in view of the above guidelines.

For use as an antibacterial agent, the rhodirubin compositions are in general administered so that the concentration of active ingredient is greater than the minimum inhibitory concentration for the particular organism being treated.

The following examples are provided for illustrative purposes only and are not intended to limit the scope of the invention.

EXAMPLE 1

A nutrient medium having the following composition was prepared:

| | | |
|---|---|---|
| Potato starch | 1 | % (w/v %) |
| Glucose | 1 | % |
| "Prorich" (soybean powder) | 1.5 | % |
| $K_2HPO_4$ | 0.1 | % |
| $MgSO_4 \cdot 7H_2O$ | 0.1 | % |
| NaCl | 0.3 | % |
| Mineral* | 0.125 | % (pH 7.4) |

*Mineral is consisted of as follows:

| | |
|---|---|
| $CuSO_4 \cdot 7H_2O$ | 2.8 g. |
| $FeSO_4 \cdot 7H_2O$ | 0.4 g. |
| $MnCl_2 \cdot 4H_2O$ | 3.2 g. |
| $ZnSO_4 \cdot 7H_2O$ | 0.8 g. |

-continued

| |
|---|
| in 500 ml. of water. |

Fifty ml. of this medium was sterilized in a 500 ml.-flask, inoculated with a loop from the agar slant of *Streptomyces galilaeus* (ATCC 31133) and incubated at 28° C. for 48 hours on a rotary shaker (230 rpm) to obtain the seed culture.

The following medium was then prepared:

| | | |
|---|---|---|
| Potato starch | 2 | % (w/v %) |
| Glucose | 2 | % |
| "Nisshin toast" (defatted soybean) | 2 | % |
| Yeast extract | 0.5 | % |
| NaCl | 0.25 | % |
| $CaC0_3$ | 0.3 | % |
| Mineral* | 0.125 | % (pH 7.4) |
| *Mineral is consisted of as follows: | | |
| $CuSO_4 . 5H_2O$ | 1.25 g. | |
| $MnCl_2 . 4H_2O$ | 1.25 g. | |
| $ZnSO_4 . 7H_2O$ | 1.25 g. | |
| in 500 ml. of water. | | |

Two ml. of said seed culture was then inoculated into 100 ml. of the previously sterilized medium described immediately above in a 500 ml.-flask. Fermentation was carried out at 28° C. on a rotary shaker (230 rpm), and the production of rhodirubin attained a maximum after 4 days. The broth was filtered to separate mycelial cake and filtrate. One-half volume of chloroform was added to the filtrate and the extraction was carried out twice. Acetone was added to the mycelial cake (2 L. of acetone/1 kg. of wet cake) and the extraction was carried out twice, after which the acetone was removed by evaporation under reduced pressure. One-half volume of chloroform was added to the residue and the extraction was carried out twice. The chloroform extracts obtained were combined with the chloroform extracts from the filtrate and concentrated under reduced pressure to obtain a tar-like substance. Said substance was dissolved in a small amount of ethyl acetate, and a precipitate was formed by the dropwise addition of this solution into 10 volumes of n-hexane (4.5 g. of red crude powder was obtained). This crude powder was dissolved in 30 ml. of a mixture of toluene and methanol (50:1) (v/v), applied onto a column (3 × =cm.) filled with 100 g. of silica gel which equilibrated with the same mixture, and rhodirubin B and then rhodirubin A were eluted. Each eluate was dried under reduced pressure to obtain 27 mg. of crude rhodirubin A and 60 mg. of crude rhodirubin B.

EXAMPLE 2

Crude rhodirubin A (27 mg.) obtained in Example 1 was chromatographed on a thin layer plate (Merck $F_{254}$, solvents: chloroform:methanol - 10:1 (v/v) to remove impurities including rhodirubin B and, after dissolving in 2 ml. of methanol, the active fraction was chromatographed onto a Sephadex LH-20 column (1 × 70 cm.). The eluate thus obtained was concentrated and precipitated with n-hexane to obtain 16.5 mg. of purified rhodirubin A as a red powder. Ten mg. of this red powder was dissolved in a mixture of 200 μl. dry acetone and 70 μl. dry methanol, and there was added 10 μl. of 3N HCl-methanol solution. After agitation for 1 minute, a precipitate was formed by the addition of 10 volumes of diethyl ether. The precipitate was collected by filtration and dried to give 7.2 mg. of rhodirubin A HCl salt.

EXAMPLE 3

Eighty mg. of crude rhodirubin B obtained in Example 1 was purified according to the same method as described in Example 2 to give 63.4 mg. of rhodirubin B as a red powder.

EXAMPLE 4

According to the same general method as described in Example 1, 2 and 3, the following microorganisms were cultivated to obtain rhodirubin A and B in the indicated yields.

| Microorganisms | Yield of rhodirubin (mg.) A | B |
|---|---|---|
| *Streptomyces galilaeus* ATCC 14949 | 23 | 14 |
| *Streptomyces cinereoruber* ATCC 19740 | 16 | 5 |
| *Streptomyces purpurascens* ATCC 25489 | 11 | 7 |
| *Streptomyces antibioticus* ATCC 8663 | 8 | 10 |
| *Streptomyces* sp. ME 505-HEI ATCC 31273 | 21 | 48 |

We claim:

1. An anthracycline glycoside of the general formula

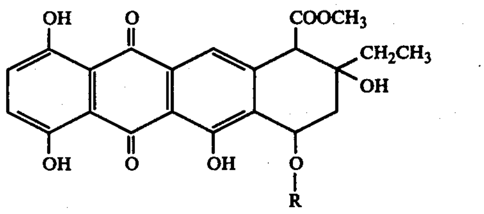

I wherein R represents

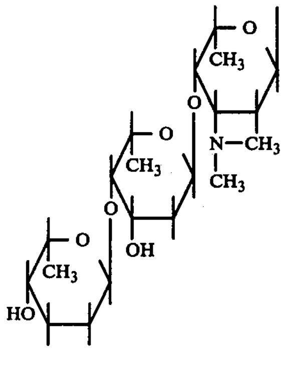

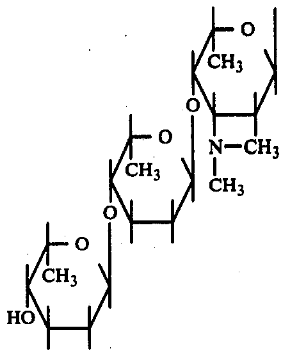

or a non-toxic acid addition salt or deoxyribonucleic acid complex thereof.

2. The anthracycline glycoside rhodirubin A of the formula

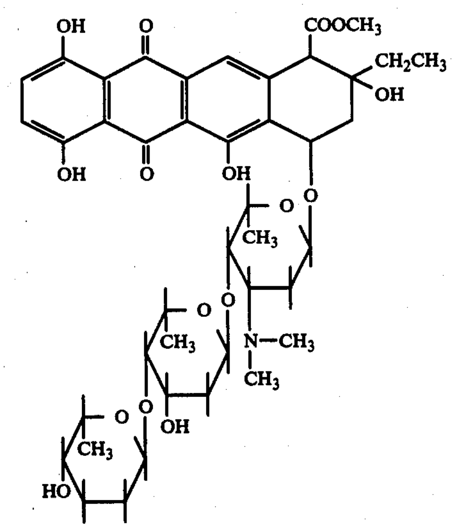

or a non-toxic acid addition salt or deoxyribonucleic acid complex thereof.

3. The anthracycline glycoside rhodirubin A of the formula

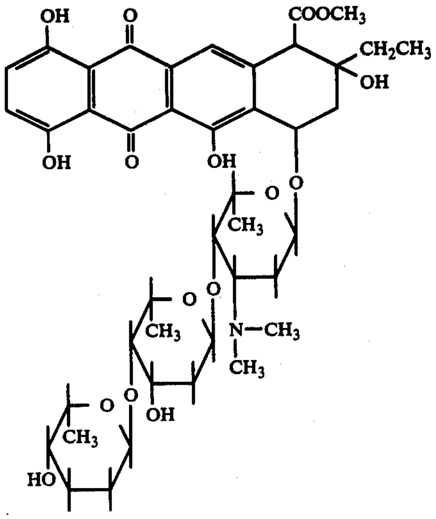

or a non-toxic acid addition salt thereof.

4. The hydrochloride salt of the anthracycline glycoside of claim 3.

5. The anthracycline glycoside rhodirubin B of the formula

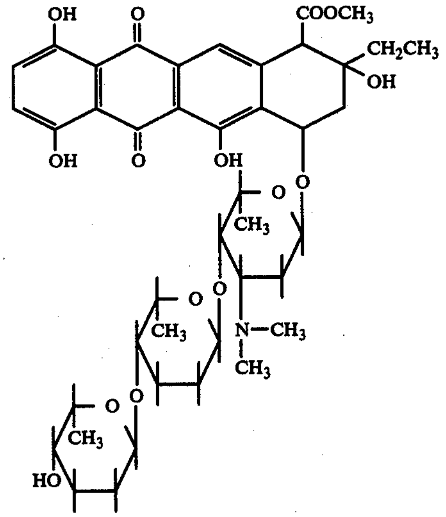

or a non-toxic acid addition salt or deoxyribonucleic acid complex thereof.

6. The anthracycline glycoside rhodirubin B of the formula

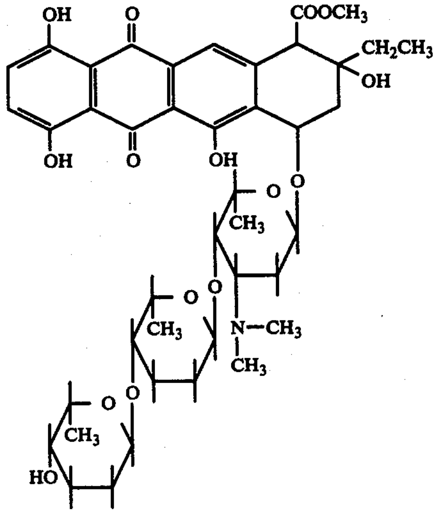

or a non-toxic acid addition salt thereof.

7. The hydrochloride salt of the anthracycline glycoside of claim 6.

* * * * *